(12) United States Patent
Matsuo et al.

(10) Patent No.: US 8,263,770 B2
(45) Date of Patent: Sep. 11, 2012

(54) ALUMINUM CHELATE COMPLEX FOR ORGANIC EL MATERIAL

(75) Inventors: Shinji Matsuo, Kitakyushu (JP); Hiroshi Miyazaki, Kitakyushu (JP); Taishi Tsuji, Tsurugashima (JP)

(73) Assignees: Nippon Steel Chemical Co., Ltd., Tokyo (JP); Pioneer Corporation, Tokyo (JP)

( * ) Notice: Subject to any disclaimer, the term of this patent is extended or adjusted under 35 U.S.C. 154(b) by 269 days.

(21) Appl. No.: 12/820,336

(22) Filed: Jun. 22, 2010

(65) Prior Publication Data

US 2010/0256377 A1    Oct. 7, 2010

Related U.S. Application Data

(62) Division of application No. 10/566,725, filed as application No. PCT/JP2004/011334 on Aug. 6, 2004, now abandoned.

(30) Foreign Application Priority Data

Aug. 7, 2003  (JP) .................. 2003-289309

(51) Int. Cl.
*C07F 5/06* (2006.01)
*C07D 215/30* (2006.01)
(52) U.S. Cl. ............................ 546/10; 546/7
(58) Field of Classification Search ............. 546/10, 546/7
See application file for complete search history.

(56) References Cited

U.S. PATENT DOCUMENTS

| | | |
|---|---|---|
| 5,141,671 A | 8/1992 | Bryan et al. |
| 5,150,006 A | 9/1992 | Van Slyke et al. |
| 5,484,922 A | 1/1996 | Moore et al. |
| 6,602,618 B2 | 8/2003 | Watanabe et al. |
| 6,617,051 B1 | 9/2003 | Higashi et al. |
| 6,656,608 B1 | 12/2003 | Kita et al. |
| 2001/0052751 A1 | 12/2001 | Wakimoto et al. |
| 2003/0129452 A1 | 7/2003 | Tsuji et al. |

FOREIGN PATENT DOCUMENTS

| | | |
|---|---|---|
| EP | 1013740 A2 | 6/2000 |
| JP | 5-198378 A | 8/1993 |
| JP | 5-214332 A | 8/1993 |
| JP | 6-172751 A | 6/1994 |
| JP | 2003-142264 A | 5/2003 |
| WO | 00/41443 A1 | 7/2000 |

*Primary Examiner* — Charanjit Aulakh
(74) *Attorney, Agent, or Firm* — Birch, Stewart, Kolasch & Birch, LLP

(57) ABSTRACT

This invention provides an organic EL material useful for the emissive layer of an organic EL element which deteriorates little in luminance when operated over a prolonged period of time and shows excellent durability. The material is an aluminum chelate complex which is represented by general formula (1) in which $Ar_1$ is a mono- or bicyclic arylene group, $Ar_2$ is a mono- or bicyclic aryl group, $R_1$-$R_6$ are hydrogen or hydrocarbon groups containing 1-8 carbon atoms and contains a compound represented by general formula (1) in which $Ar_2$ is a halogen as an impurity in an amount of 350 wt ppm or less.

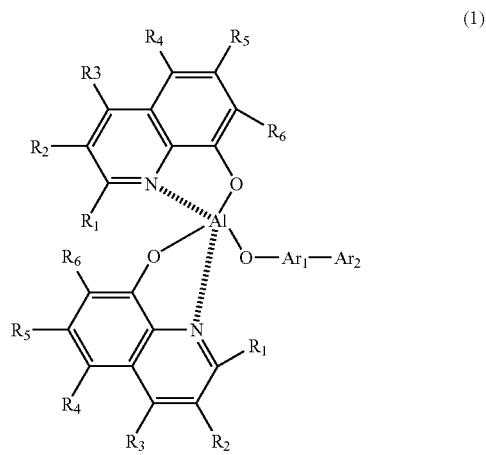

(1)

7 Claims, 1 Drawing Sheet

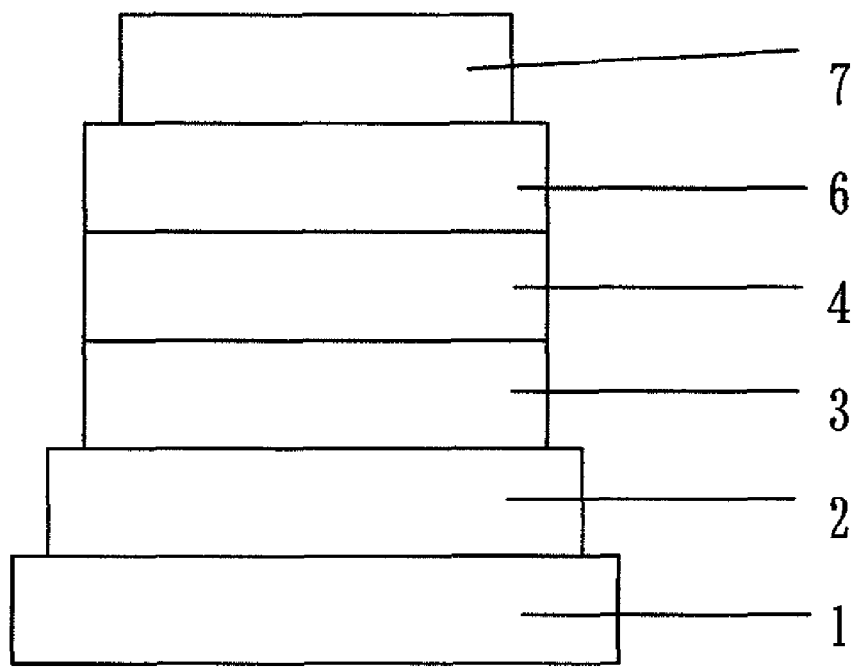

ALUMINUM CHELATE COMPLEX FOR ORGANIC EL MATERIAL

This application is a Divisional of application Ser. No. 10/566,725 filed on Feb. 2, 2006 now abandoned and for which priority is claimed under 35 U.S.C. §120. Application Ser. No. 10/566,725 is the national phase of PCT International Application No. PCT/JP04/11334 filed on Aug. 6, 2004 under 35 U.S.C. §371. This application also claims priority under 35 U.S.C. §119 to Application No. 2003-289309, filed on Aug. 7, 2003 in Japan. The entire contents of each of the above-identified applications are hereby incorporated by reference.

FIELD OF TECHNOLOGY

This invention relates to an aluminum chelate complex useful as a material to be incorporated in an organic electroluminescent element (hereinafter referred to as an organic EL element) and its emissive layer and other parts.

BACKGROUND TECHNOLOGY

An organic EL element constituting a display panel using an organic material is generally formed from a glass substrate as a display surface, an anode as a transparent electrode, plural layers of organic materials containing an organic emissive layer and a cathode consisting of a metal electrode, each prepared in thin film and stacked one upon another. The layers of organic materials contain layers capable of transporting holes such as a hole injecting layer and a hole transporting layer and layers capable of transporting electrons such as an electron transporting layer and an electron injecting layer in addition to an organic emissive layer and organic EL elements comprising such layers of organic materials have also been proposed. An inorganic compound may as well constitute an electron injecting layer.

When an electrical field is applied to an organic EL element comprising an organic emissive layer and an electron or hole transporting layer, holes are injected from the anode and electrons from the cathode. These electrons and holes recombine together in the organic emissive layer to form excitons which return to the ground state with emission of light and an organic EL element utilizes this emission of light. The emissive layer is often doped with a colorant as a guest material to raise the luminous efficiency or to operate the element stably.

In recent years, the use of phosphorescent materials besides fluorescent materials in the emissive layer has been proposed. In the emissive layer of an organic EL element, the probability of generating singlet excitons and triplet excitons after recombination of electrons and holes is thought to be 1:3 and an element utilizing phosphorescence by triplet excitons as well is thought to attain luminous efficiency three to four times greater than that of an element utilizing fluorescence by singlet exictons.

On the other hand, for the purposes of reducing the power requirement and improving the luminous efficiency and operating stability of an organic EL element, a proposal has been made to provide a hole blocking layer between the organic emissive layer and the cathode to restrict the migration of holes from the organic emissive layer. This hole blocking layer accumulates holes efficiently inside the emissive layer thereby improving the probability of recombination of holes with electrons and raising the luminous efficiency. Phenanthroline derivatives and triazole derivatives have been reported to be effective as hole-blocking materials.

Patent literature 1: JP4-206685A
Patent literature 2: JP2001-237079A
Patent literature 3: JP2001-284056A It is reported in JP04-206685A that a complex of aluminum with a hydroxyquinoline compound and a phenolic compound (hereinafter referred to as AlQ2OR) is useful as an organic EL material emitting blue light. This AlQ2OR has a structure in which one aluminum atom is complexed with two molecules of 8-hydroxyquinoline compounds and one molecule of a phenolic compound. In an example disclosed in JP04-206685A, AlQ2OR is incorporated in the electron transporting layer to emit light.

A phosphorescent or fluorescent organic EL element reported in JP2001-237079A has AlQ2OR in the hole blocking layer. Further, a phosphorescent organic EL element reported in JP2002-284056A has a hole blocking layer comprising AlQ2OR between the emissive layer containing a phosphorescent material and the electron transporting layer.

A compound cited in JP2001-237079A and JP2001-284056A for AlQ2OR is (1,1'-biphenyl)-4-olato)bis(2-methyl-8-quinolinolato-N1,O8)aluminum (hereinafter referred to as BA1q) obtained from 2-methyl-8-hydroxyquinoline as a hydroxyquinoline compound and 4-phenyphenol as a phenolic compound. Although BA1q shows excellent durability, it has a shortcoming of inferior hole-blocking ability as its ionization potential (Ip) is not sufficiently large. Consequently, in the cases where BA1q is used in the hole blocking layer and tris(8-hydroxyquinolinato-N1,O8)aluminum (hereinafter referred to as Alq3) is used in the electron transporting layer, it is the electron transporting layer that emits light. In an organic EL element utilizing red phosphorescence, the emission of light (green) by Alq3 leads to degradation of chromaticity. Now, it has been found in some cases that, in an organic EL element whose emissive layer comprises a phosphorescent material as a guest material, the use of AlQ2OR as a host material is capable of attaining a long operating life while maintaining good luminous characteristics.

However, the life of an element using AlQ2OR disperses a great deal and this has become a large obstacle in putting an element of this kind into practical use. The cause of this dispersion of life has not been elucidated at all. As a result, there has not been a clue for setting up guidelines not only for the control of materials essential for the manufacture of highly reliable commercial elements but also for improvement of life.

DISCLOSURE OF THE INVENTION

Problems to be Solved by the Invention

An object of this invention is to elucidate the causes affecting the life of an organic EL element comprising AlQ2OR, offer remedial means, set up a guideline for the control of materials essential for the manufacture of highly reliable commercial elements and provide an organic EL material which constitutes an organic EL element capable of manifesting excellent performance with little deterioration of luminance with passage of time, excellent reliability and high product quality acceptable to practical use and an organic EL element utilizing said organic EL material.

Means to Solve the Problems

The inventors of this invention have conducted extensive studies in the development of commercially viable organic EL materials comprising AlQ2OR, found that AlQ2OR prepared by the usual method contains specific impurities, clarified the relationship between the content of these impurities and the durability of an organic EL element and completed this invention.

This invention relates to an aluminum chelate complex for an organic EL material represented by general formula (1) in which a compound represented by general formula (2) is present as an impurity in an amount of 350 wt ppm or less.

[C1]

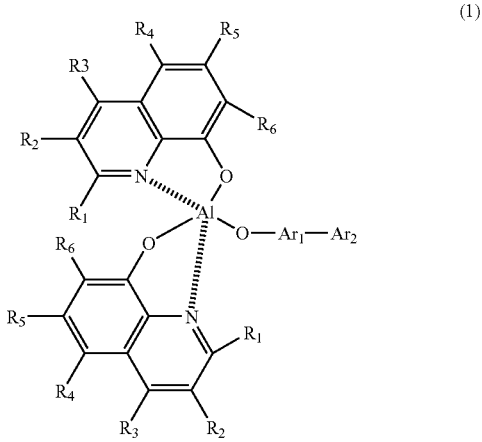

(1)

[C2]

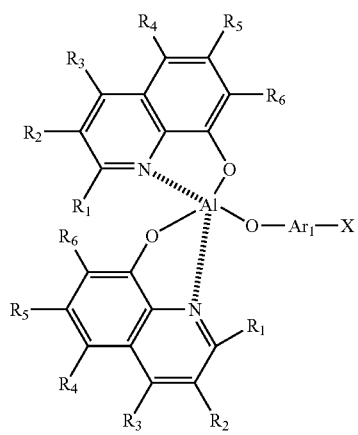

(2)

In general formulas (1) and (2), $Ar_1$ is a mono- or bicyclic arylene group, $Ar_2$ is a mono- or bicyclic aryl group, the total number of aromatic rings in $Ar_1$ and $Ar_2$ is 2 to 4, and where $Ar_1$ or $Ar_2$ contains 2 or more aromatic rings, these aromatic rings may be condensed. The groups $R_1$-$R_6$ are independently hydrogen or hydrocarbon groups containing 1-8 carbon atoms. The group X is a halogen. In general formulas (1) and (2), the same symbols mean the same thing.

Here, the arylene and aryl groups or $Ar_1$ and $Ar_2$ need to be linked together directly, that is, $Ar_2$ is substituted at the nucleus of $Ar_1$. The groups $Ar_1$ and $Ar_2$, when represented respectively by H—$Ar_1$—H and $Ar_2$—H, are exemplified by benzene, naphthalene, biphenyl and their alkyl-substituted derivatives. The substituent alkyl groups here are preferably those containing 1-6 carbon atoms (lower alkyl groups) and the number of substituents is preferably 3 or less. More preferably, $Ar_1$ is naphthylene or phenylene and $Ar_2$ is naphthyl or phenyl. The total number of aromatic rings in $Ar_1$ and $Ar_2$ is preferably 2 or 3.

In general formulas (1) and (2), the groups $R_1$-$R_6$ are independently hydrogen or hydrocarbon groups containing 1-8 carbon atoms such as alkyl and alkenyl and alkyl groups containing 1-3 carbon atoms are preferred. However, hydrocarbon groups containing aryl groups or aryl-containing groups are excluded. The group X is preferably Br, I or Cl.

The aforementioned aluminum chelate complex can be obtained by reacting aluminum isopropoxide successively with a quinolinol derivative and a phenolic compound represented by HO—$Ar_1$—$Ar_2$. This aluminum chelate complex can be used as the aforementioned host material of the emissive layer in an organic EL element comprising an organic emissive layer between the anode and the cathode.

This invention will be described below in detail.

An organic EL material consisting of an aluminum chelate complex or A1Q2OR represented by general formula (1) is used in an organic EL element, preferably as a host material in the emissive layer. Regarding the method for preparing A1Q2OR, aluminum isopropoxide is reacted successively with a quinolinol derivative and a phenolic compound in ethanol as reported in JP04-206685A.

A quinolinol derivative to be used as a lignad in the aforementioned reaction can be synthesized by the Ullmann reaction from an arylamine compound and a haloaryl compound. However, when this derivative is a compound in common use such as 8-hydroxyquinoline, a commercially available material may be used for it.

A phenolic compound can be synthesized by the known cross-coupling reactions such as the following; the Suzuki coupling reaction of an organic boron compound with a halide or a triflate compound ($Ar_1$+ or $Ar_1$—OTf+$Ar_2$B$(OH)_2$→ $Ar_1$—$Ar_2$), the reaction using a diazonium salt ($Ar_1$+$Ar_2$—$N_2$Cl→$Ar_1$—$Ar_2$), the Ullmann reaction of halides in the presence of a copper catalyst ($Ar_1$—X+$Ar_2$—X+$Ar_1$—$Ar_2$), the reaction involving the use of a Grignard reagent and a variety of organometallic compounds ($Ar_1$—X+$Ar_2$—MgX→$Ar_1$—$Ar_2$, $Ar_1$—X+$Ar_2$—Li→$Ar_1$—$Ar_2$, $Ar_1$—X+$Ar_2$—ZnX→$Ar_1$—$Ar_2$, $Ar_1$—X+$Ar_2$—SnMe$_3$→$Ar_1$-$Ar_2$). In the aforementioned reaction equations, $Ar_1$ and $Ar_2$ denote aromatic groups. However, the reactions in which a hydroxyaryl halide is formed as a byproduct or remains unreacted are suitable for this invention.

A phenolic compound can preferably be synthesized by the reaction of a compound represented by HO—$Ar_1$—X with a compound represented by $(Ar_2)_a$—Y. Here, $Ar_1$, $Ar_2$ and X are defined the same as in general formulas (1) and (2). The group Y is Cu, X, Li, B(OH)$_2$, MgX, ZnX or SnMe$_3$, X is a halogen and a is an integer of 1-10 corresponding to the valence of Y. The reaction product is a phenolic compound represented by HO—$Ar_1$—$Ar_2$ or its decomposition product. As this reaction is usually carried out in an organic solvent, the reaction product is extracted with water under an acidic condition thereby transferring the target phenolic compound into the organic phase and the halogen-containing compound into the aqueous phase. Thus, it has been generally considered that the target phenolic compound here can be purified by washing with water alone and has been purified in this manner.

Now, the phenolic compound thus obtained is used as a raw material for an aluminum chelate complex. As the reaction for the synthesis of an aluminum chelate complex yields alcohols as byproducts, the product is also purified by washing and the like upon completion of the reaction. For this reason, it has not been considered necessary to exercise sufficient care in the purification of the phenolic compound.

However, it has been found that a halogen-containing compound represented by HO—$Ar_1$—X remains in an amount of several % to a little over 10% in the synthesis of a phenolic compound represented by HO—Ar$_1$—Ar$_2$ and this residual halogen-containing compound is difficult to remove by extraction with water or by washing with water alone in the purification of the phenolic compound. Moreover, when A1Q2OR represented by general formula (1) is synthesized from a phenolic compound containing the aforementioned halogen-containing compound, the reaction product contains a byproduct represented by general formula (2) (hereinafter referred to as A1Q2X) and this byproduct is difficult to remove sufficiently by a generally practiced procedure of washing with alcohol in the purification of A1Q2OR.

Still more, it has been found that the use of an aluminum chelate complex containing the aforementioned byproduct in excess of a certain amount in the manufacture of an organic EL element causes a marked increase in the rate of deterioration of luminance, probably for the following reason. In the manufacture of an organic EL element, these materials are mostly vacuum-deposited on the organic layer on a substrate and A1Q2X behaves similarly to A1Q2OR in the vacuum deposition and becomes incorporated in the organic layer of an organic EL element.

It has now been found that the rate of deterioration in luminance can be reduced to a level which is tolerable in practical use if the content of A1Q2X as an impurity in A1Q2OR is reduced to 350 ppm or less and that the manufacture of organic EL elements with a sufficiently long light-emitting life in practical use is feasible if the content of A1Q2X in A1Q2OR is reduced to a trace or below 100 ppm.

The content of A1Q2X can be reduced to 350 ppm or less by the following methods: 1) in the synthesis of a phenolic compound represented by HO—Ar$_1$—Ar$_2$, the separation and purification of the product are carried out not merely by washing with water and separation by distillation but by a combination of these procedures with another such as recrystallization from an organic solvent; 2) in the synthesis of an aluminum chelate complex by successive reaction of an aluminum alcoholate, a quinolinol derivative and a phenolic compound, the separation and purification after completion of the reaction are carried out not by washing with alcohol alone but by a combination of washing with alcohol with another procedure such as purification by sublimation; 3) a combination of the aforementioned methods 1) and 2); 4) in the synthesis of a phenolic compound represented by HO—Ar$_1$—Ar$_2$—H, the reaction of HO—Ar$_1$—X with an Ar$_2$-containing compound is carried out in such a manner as to raise the conversion of HO—Ar$_1$—X above 90% and keep the unreacted HO—Ar$_1$—X below a certain level by making the molar ratio of HO—Ar$_1$—X to the Ar$_2$-containing compound smaller than the theoretical value, raising the reaction temperature or running the reaction for a sufficiently long period of time. In particular, the aforementioned method 3) or the method involving purifying the reaction product phenolic compound represented by HO—Ar$_1$—Ar$_2$ by recrystallization and purifying the aluminum chelate complex obtained from the phenolic compound by sublimation is effective.

Halogen-containing compounds represented by HO—Ar$_1$—X can be analyzed by HPLC and the lower limit of detection of a Br compound is 0.5 wt ppm. When the content of the halogen-containing compounds is reduced to 350 ppm or less, the content of A1Q2X in the finally obtained aluminum chelate complex can be reduced to 350 ppm or less. On the other hand, the content of A1Q2X in the finally obtained aluminum chelate complex is difficult to determine directly because aluminum chelate complexes are unstable at high temperatures and decompose during passage through a column kept at high temperatures in the chromatographic analysis. However, the content of halogens can be determined by ion chromatography and this is used to calculate the content of A1Q2X. Thus, the content of A1Q2X represented by general formula (2) in this invention is calculated in this manner from the amount of X.

The quality of an aluminum chelate complex to be used for an organic EL material according to this invention is controlled preferably in the stage of production, shipping or use so that the content of a compound represented by general formula (2) is kept at 350 ppm or less.

Halogen-containing compounds formed as byproducts in the preparation of phenolic compounds or the raw materials for the preparation of complexes according to this invention can be removed by the methods in common use such as recrystallization, crystallization, distillation and adsorption and recrystallization is preferable for its simpleness and sureness. In the cases where halogen-containing compounds are formed in the preparation of quinolinol derivatives, these compounds are preferably removed by purification using the aforementioned methods. The removal of halogen-containing compounds in the quinolinol derivatives and phenolic compounds is effected to a level of 350 wt ppm or less, preferably below the lower limit of detection.

The content of A1Q2X represented by general formula (2) in the final product A1Q2OR represented by general formula (1) amounts to a level ranging from several % to a little over 10% when the quinolinol derivatives and phenolic compounds are not purified in the aforementioned manner, but this level can be reduced to $1/10$ or less by purifying these compounds by sublimation and the like.

It is possible to attain the object of this invention by performing purification surely either in the ligand stage of the quinolinol derivatives and phenolic compounds or in the final aluminum complex stage and it is preferable to perform purification in both stages.

Effect of the Invention

The use of an organic EL material prepared according to this invention provides an organic EL element which deteriorates little in luminance when operated over a prolonged period of time and shows excellent durability.

BRIEF DESCRIPTION OF THE DRAWING

FIG. 1 A drawing illustrating an example of the layered structure of an organic EL element.

EXPLANATION OF THE NUMBERS IN THE DRAWING

1 glass substrate; 2, transparent electrode (anode); 3, organic hole transporting layer; 4, organic emissive layer; 6, electron transporting layer; 7, metal electrode (cathode).

PREFERRED EMBODIMENTS OF THE INVENTION

The A1Q2ORs suitable as aluminum chelate complexes for the organic EL materials of this invention are exemplified by Compounds (11)-(23), but they are not limited to these examples.

[C3]
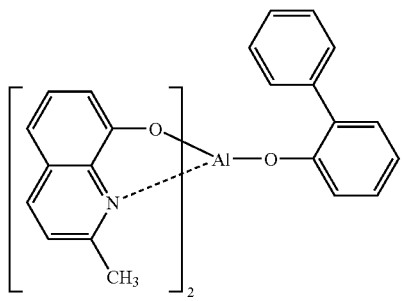
(11)
[C4]
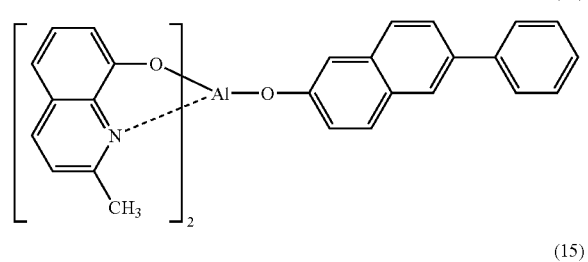
(13)
(14)
(15)
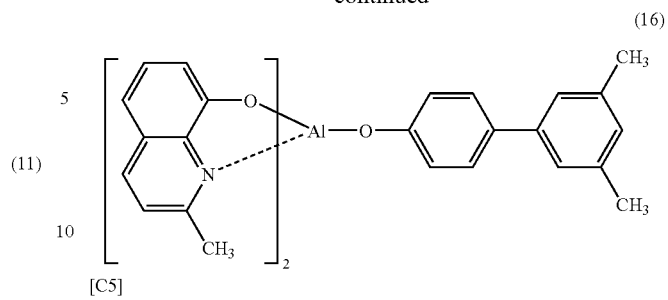
(16)
[C5]
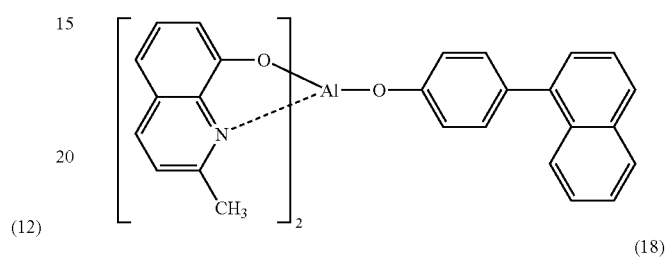
(17)
(18)
[C6]
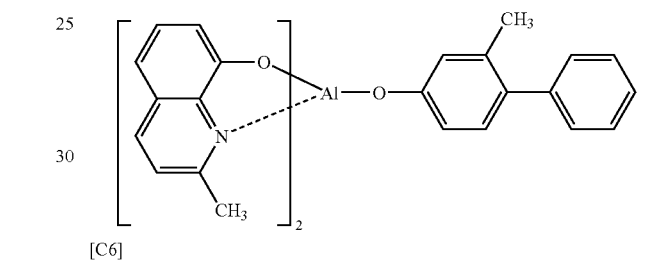
(19)
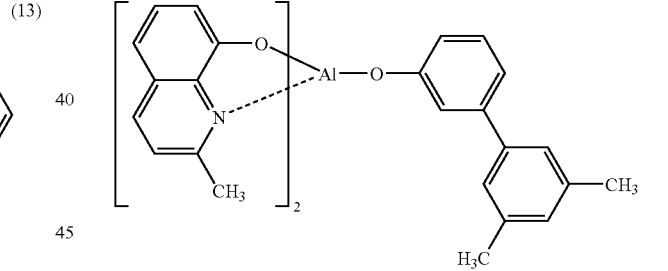
(20)
(21)

[C7]

(22)
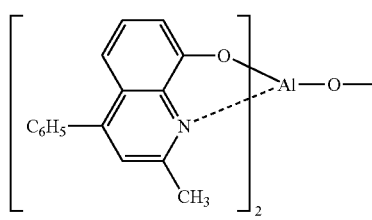

(23)
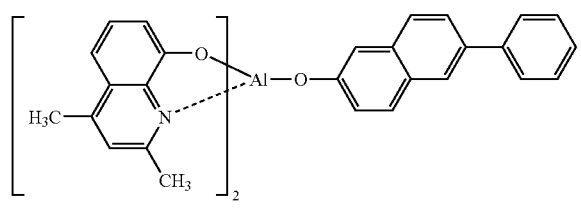

An aluminum chelate complex prepared according to this invention is used as an organic EL material. The material can be used in the electron transporting layer, hole blocking layer, emissive layer and the like of an organic El element and its use in the emissive layer is preferable. The material can be used advantageously as a host material of the emissive layer comprising a host material and a guest material. In this case, a phosphorescent organic complex of a noble metal selected from ruthenium, rhodium, palladium, silver, rhenium, osmium, iridium, platinum and gold is used as a guest material. An organic EL element comprising a host material and a guest material in its emissive layer deteriorates little in luminance with passage of time and shows excellent reliability.

The aforementioned guest materials consisting of phosphorescent organic noble metal complexes are exemplified below by Compounds (31)-(40), but they are not limited to these examples.

[C8]

(31)
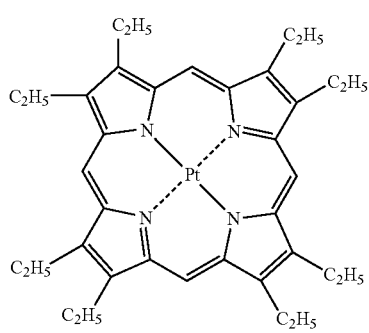

(32)
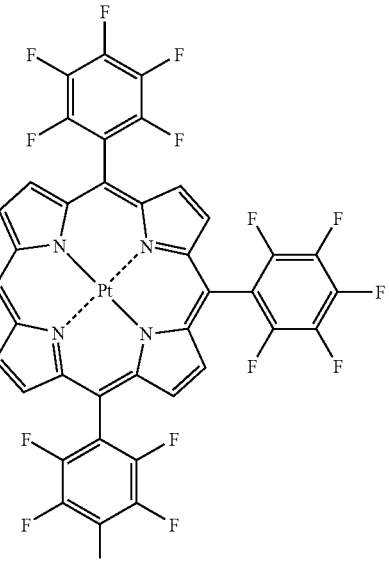

[C9]

(33)
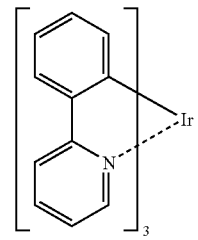

(34)
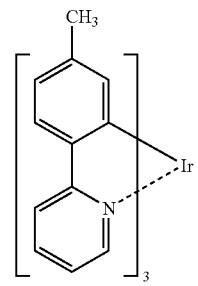

(35)
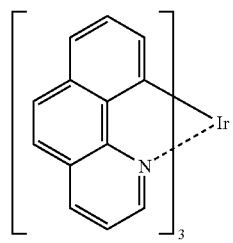

(36)
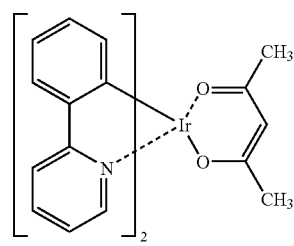

-continued

[C10]

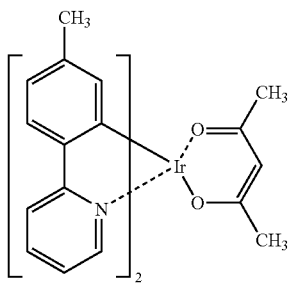
(37)

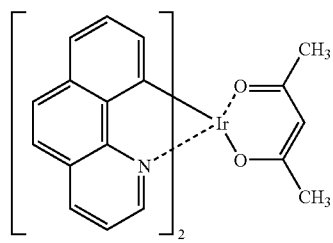
(38)

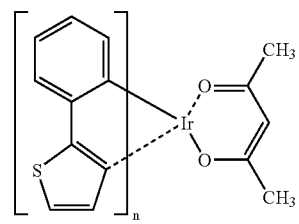
(39)

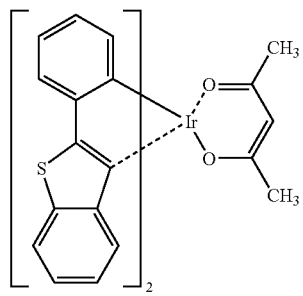
(40)

An organic El element prepared according to this invention will be described below with reference to FIG. 1 which is a cross section of the element illustrating its layered structure.

The organic EL element shown in FIG. 1 is composed of a transparent substrate 1 made from glass and the like, an anode 2, a hole transporting layer 3, an emissive layer 4, an electron transporting layer 6 and a cathode 7. This can be obtained by piling a transparent anode 2, a hole transporting layer 3 consisting of an organic compound, an emissive layer 4, an electron transporting layer 6 and a metal cathode 7 made from a material of low work function one upon another in this order on a transparent substrate 1 made from glass and the like. For example, an organic EL element has an anode made from indium tin oxide (hereinafter referred to as ITO), a hole transporting layer of 4,4'-bis(N-naphthyl-N-phenyl-amino)biphenyl (hereinafter referred to as NPB) (Ip=5.4 eV), an emissive layer containing A1Q2OR as an organic host material, an electron transporting layer of Alq3 and a cathode made from aluminum.

Besides the organic EL element shown in FIG. 1, there is another preferable organic El element which additionally has a thin electron injecting layer of $Li_2O$ and the like between the electron transporting layer 6 and the cathode 7. There is still another preferable organic EL element which has a thin hole injecting layer consisting of a porphyrin compound such as copper phthalocyanine (hereinafter referred to as CuPc) between the anode 2 and the hole transporting layer 3.

The anode 2 consists of a conductive material of large work function; for example, ITO with a thickness of 1000-3000 Å or gold with a thickness of 800-1500 Å. When gold is used as an electrode material, the electrode becomes translucent. It suffices if either of the cathode and the anode is transparent or translucent. The cathode 7 consists of a metal of small work function such as aluminum, magnesium, indium and silver and alloys thereof and its thickness is approximately 100-5000 Å.

The components in the hole transporting layer 3 may be any substances which are capable of transporting holes, for example, Compounds (41)-(66) shown below (41)

[C11]

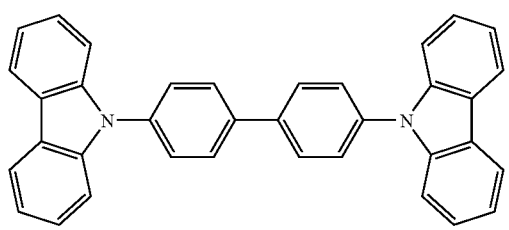

(42)
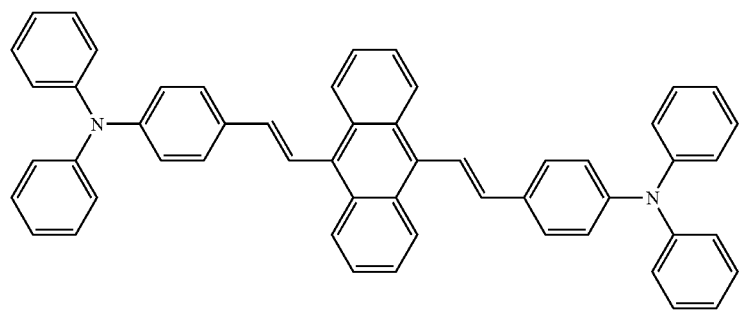
(43)
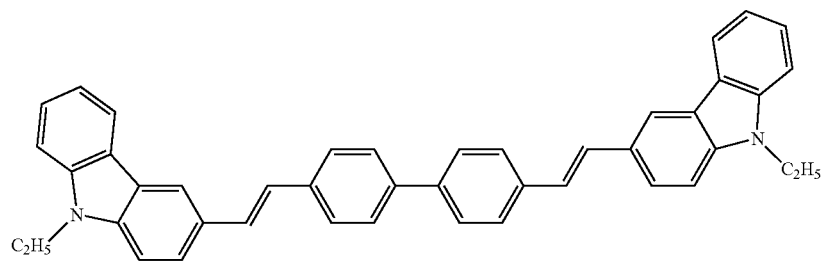
[C12]
(44)
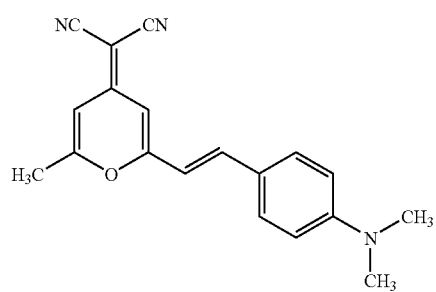
(45)
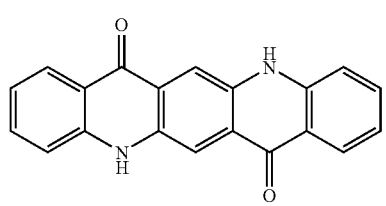
(46)
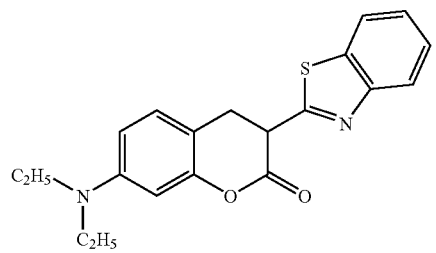
(47)
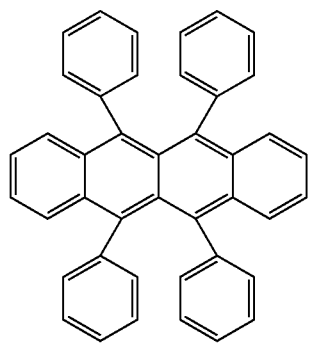
[C13]

-continued
(48)
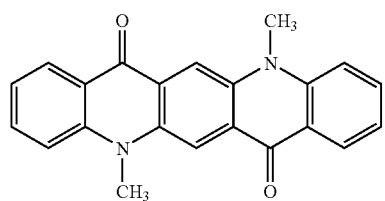
[C14]
(49)
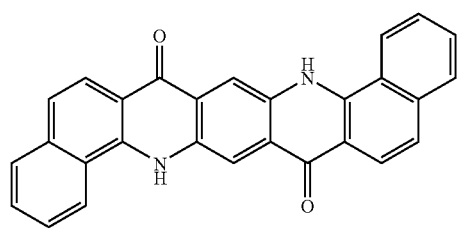
(50)
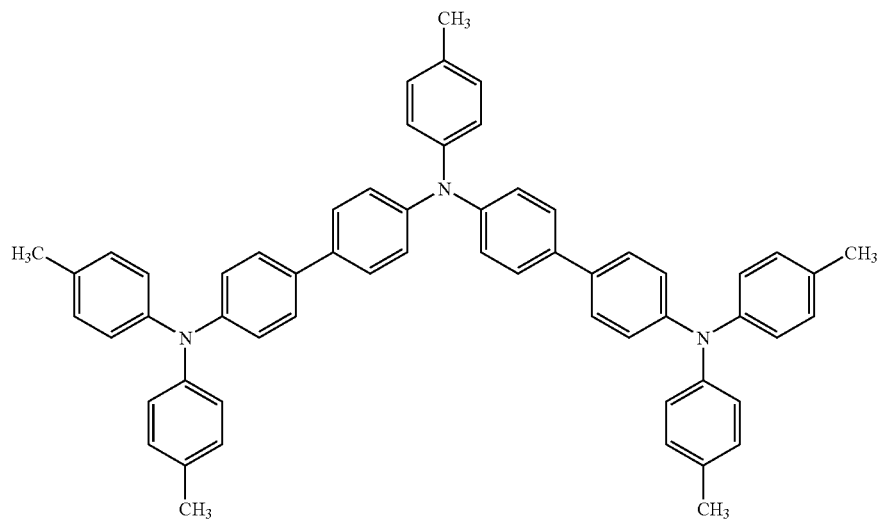
[C15]
(51)
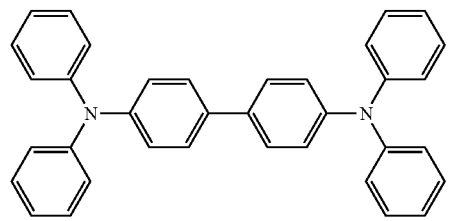
(52)
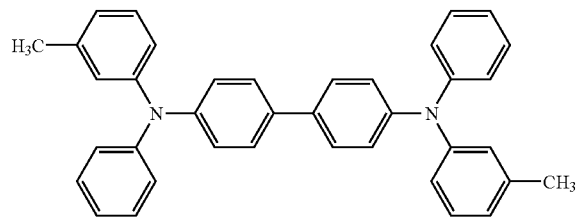
[C16]
(53)
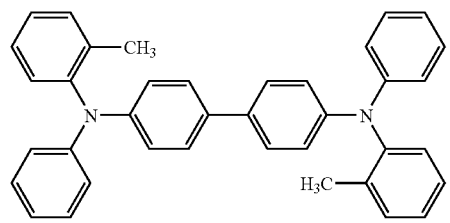
(54)
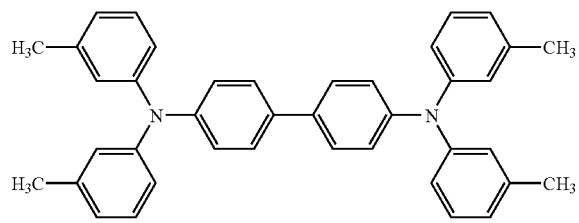
(55)
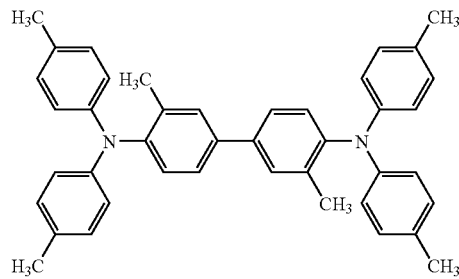
(56)
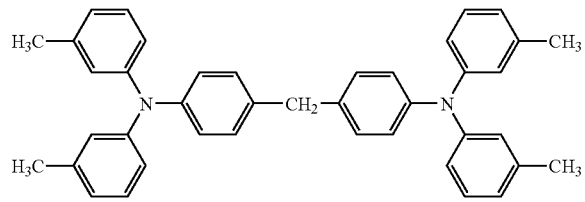

-continued
[C17]
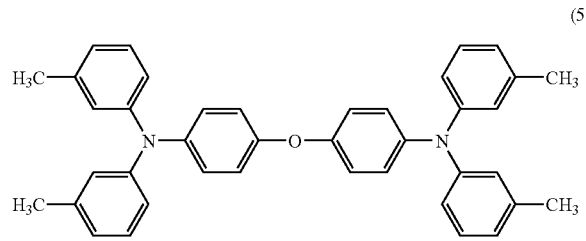
(57)
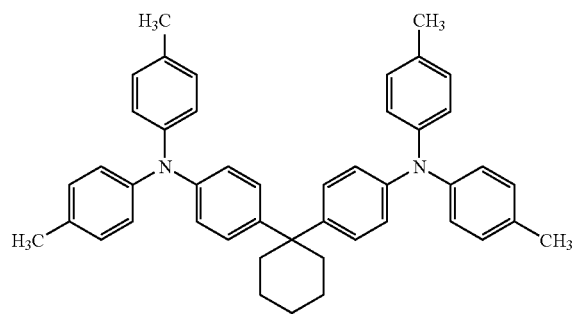
(58)
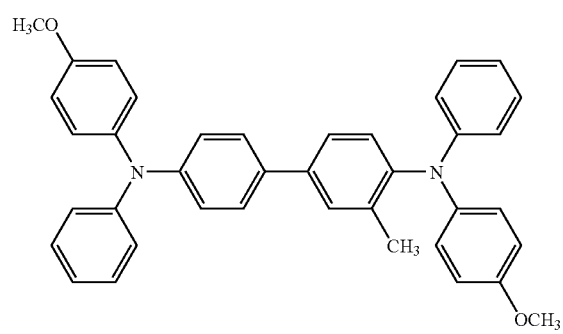
(59)
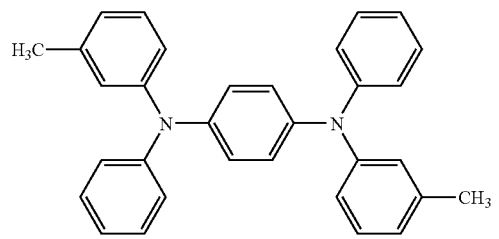
(60)
[C18]
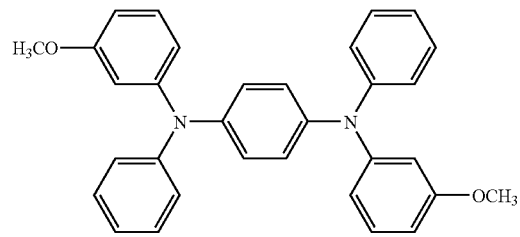
(61)
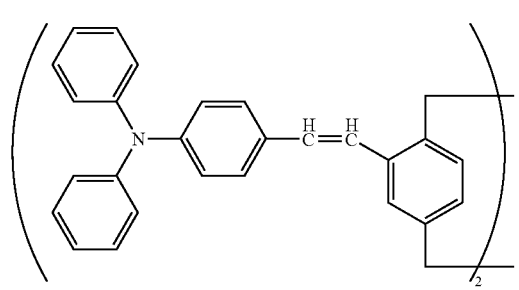
(62)
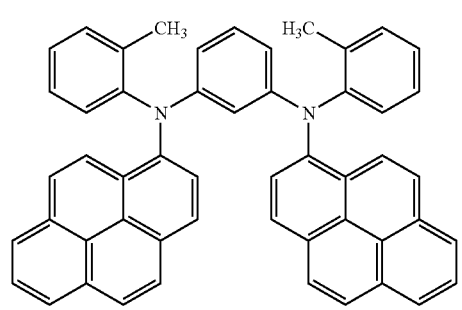
(63)
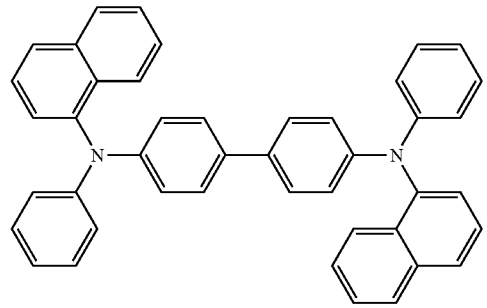
(64)

[C19]

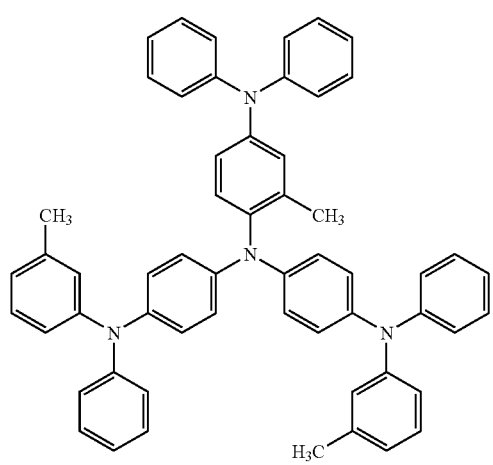
(65)

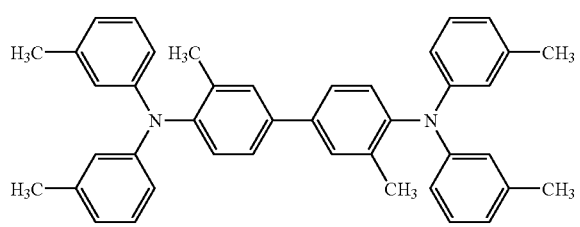
(66)

The emissive layer is composed of an aluminum chelate complex as a host material and a phosphorescent organic noble metal complex as a guest material and the aforementioned A1Q2OR is used as a host material and any one of the aforementioned organic noble metal complexes as a guest material. However, if necessary, it is allowable to incorporate a small amount of other materials to the extent that such incorporation does not damage the effect of this invention. The ratio by weight of the host material to the guest material in use is 97:3-70:30.

The material to constitute the electron transporting layer 6 is chosen from known materials, for example, Compounds (71)-(89) shown below.

[C20]

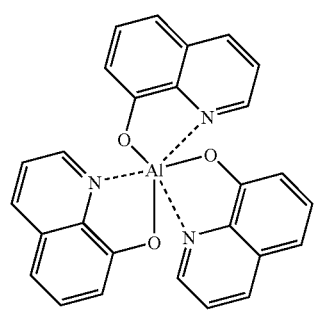
(71)

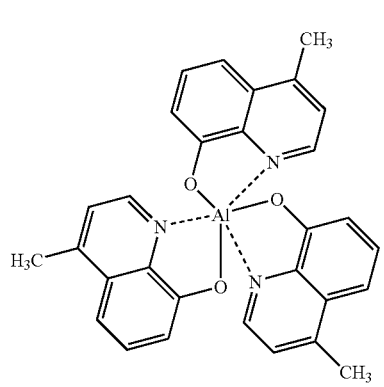
(72)

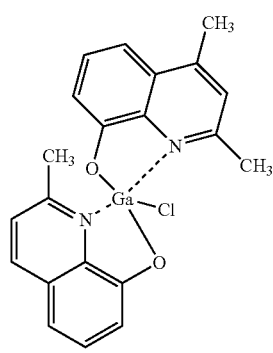
(73)

[C21]
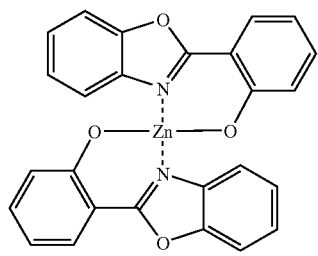
(74)
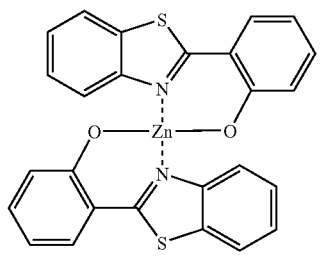
(75)
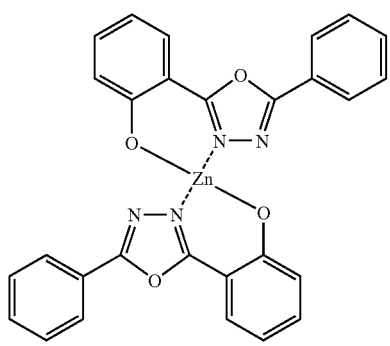
(76)
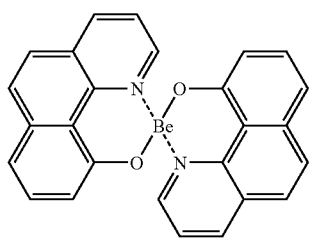
(77)
[C22]
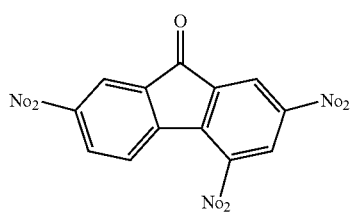
(78)
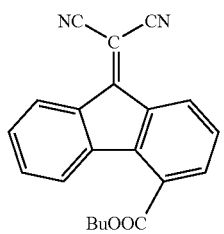
(79)
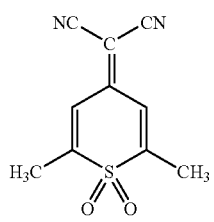
(80)
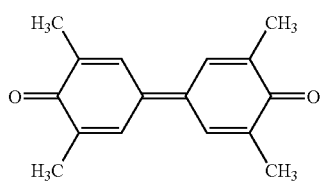
(81)

-continued
(82)
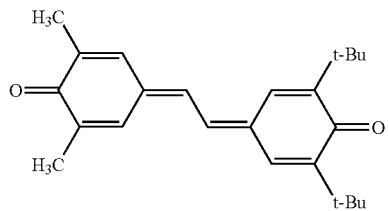
[C23]
(83)
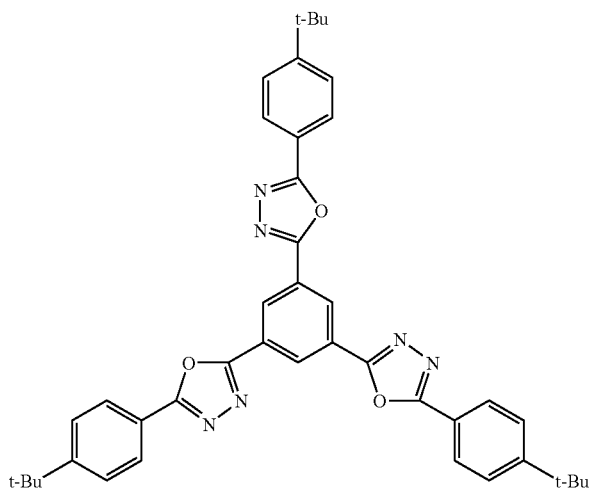
(84)
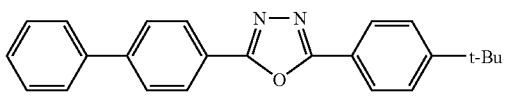
(85)
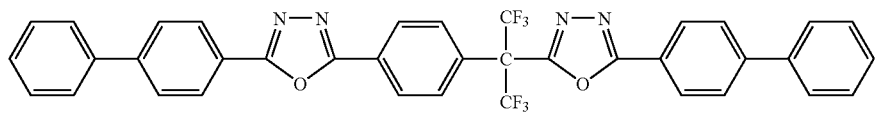
[C24]
(86)
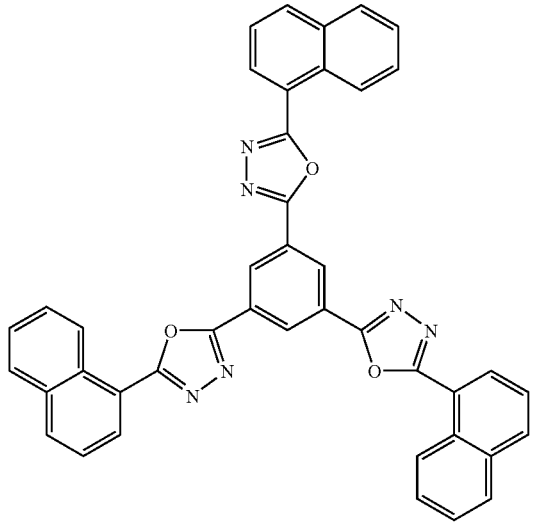

[C25]
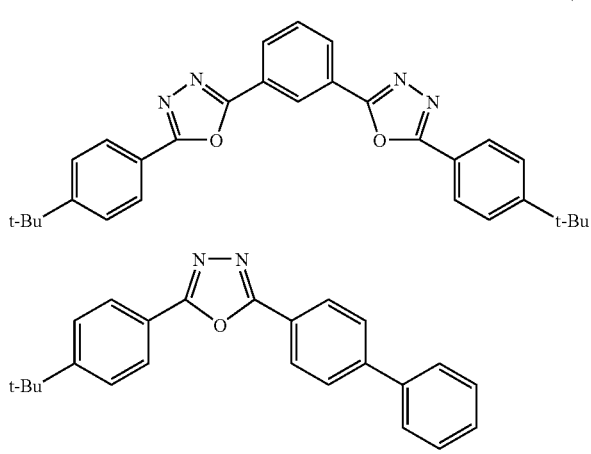
(87)
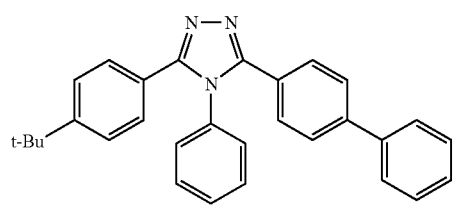
(88)
(89)
In the aforementioned compounds, t-Bu denotes tertiary butyl group. The aluminum chelate complexes shown below or Compounds (90)-(125) are organic materials capable of transporting electrons.
[C26]
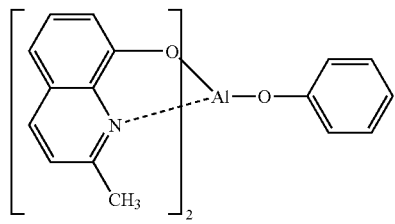
(90)
[C27]
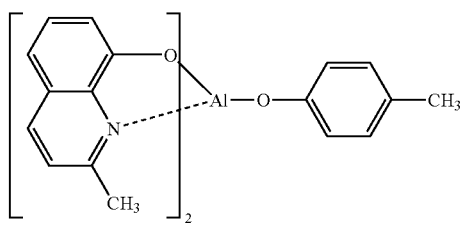
(91)
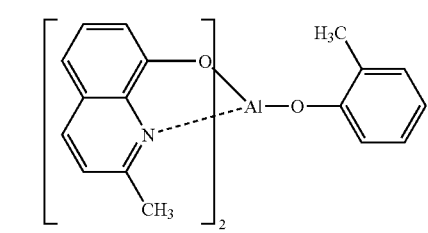
(92)
-continued
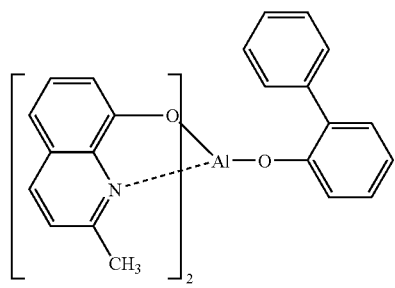
(93)
(94)
[C28]
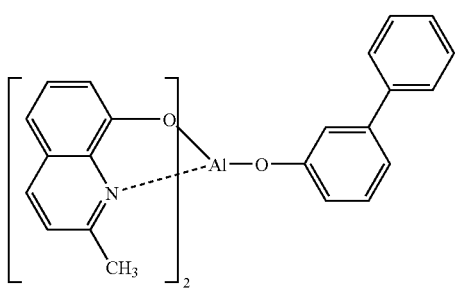
(95)

(96) 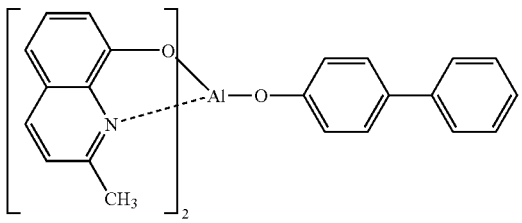
(97) 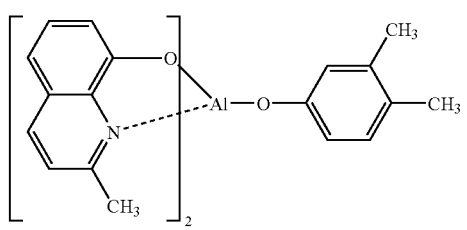
[C29]
(98) 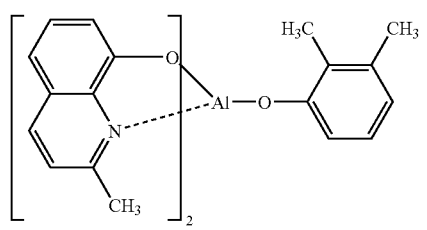
(99) 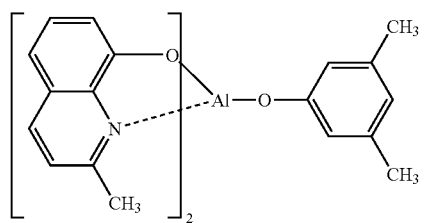
(100) 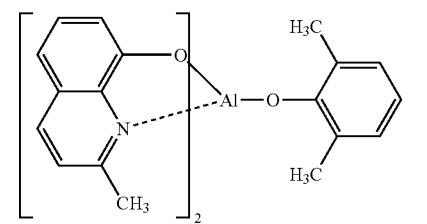
(101) 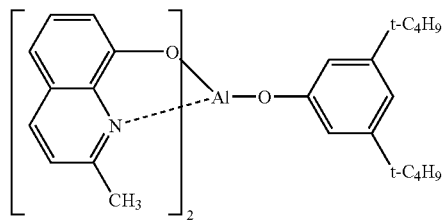
[C30]
(102) 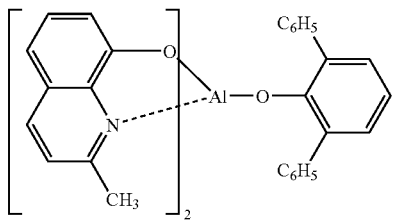
(103) 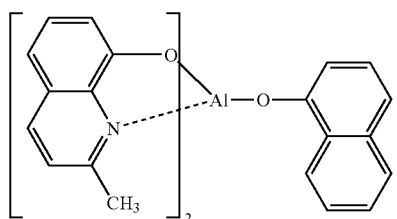
(104) 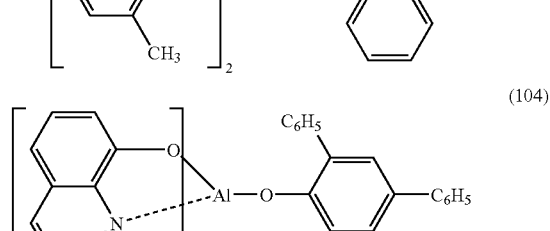
(105) 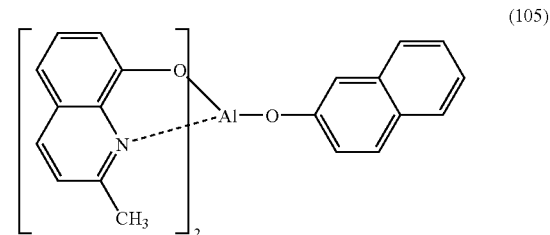
[C31]
(106) 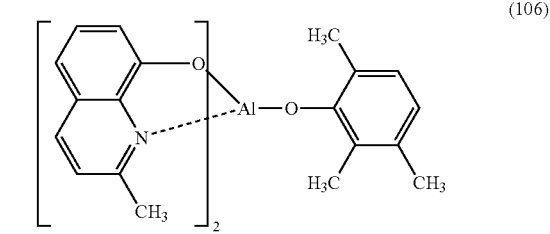
(107) 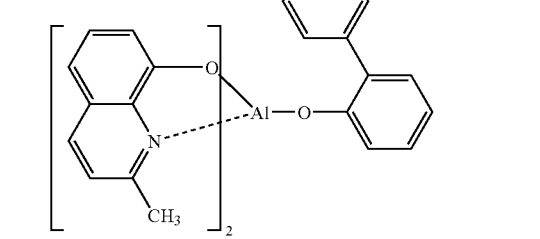

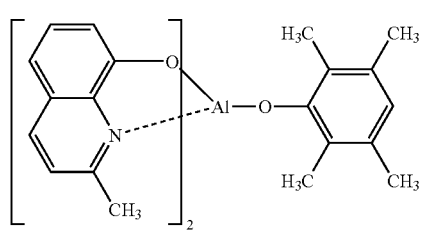 (108)
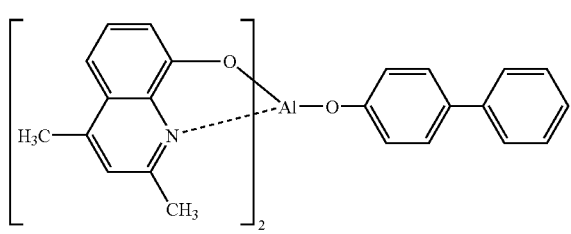 (109)
[C32]
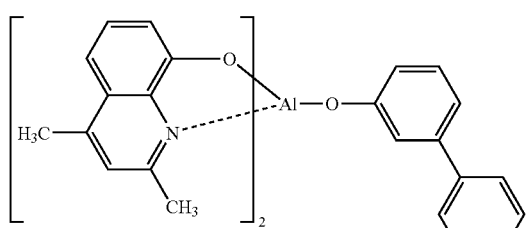 (110)
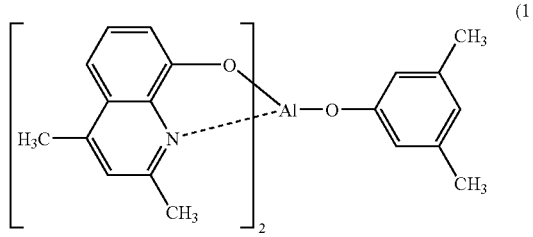 (111)
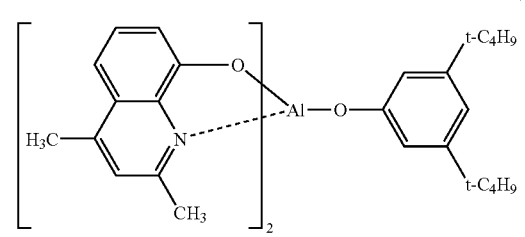 (112)
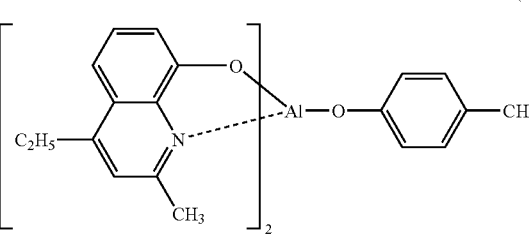 (113)
[C33]
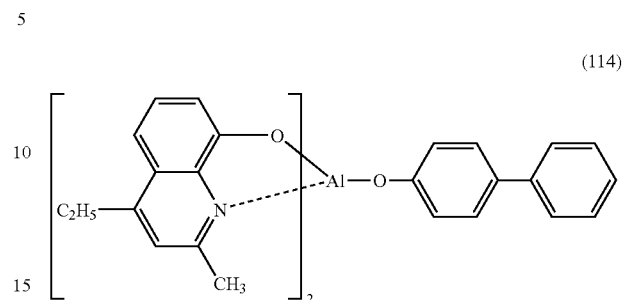 (114)
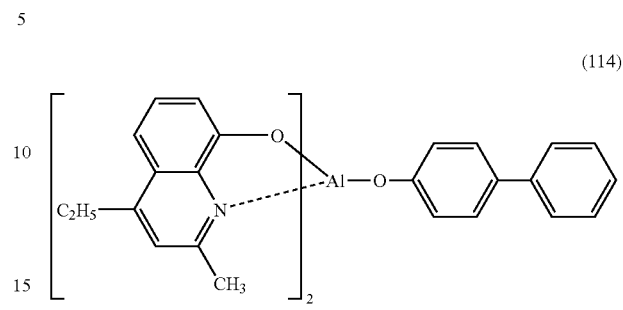 (115)
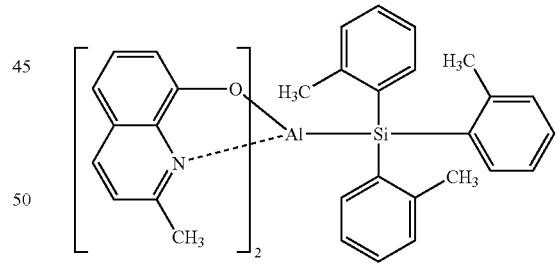 (116)
(117)
[C34]
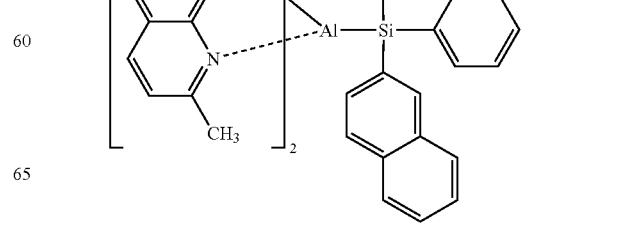 (118)

(119)
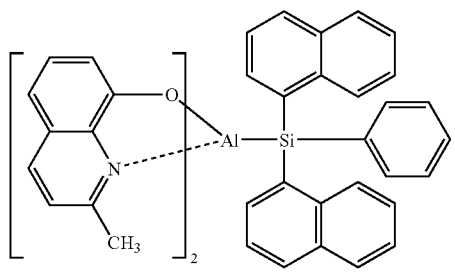
(120)
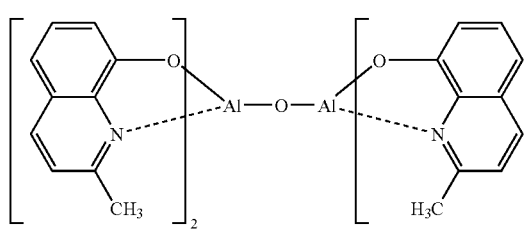
[C35]
(121)
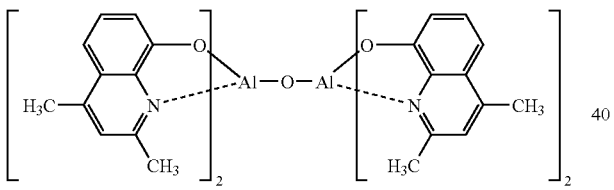
(122)
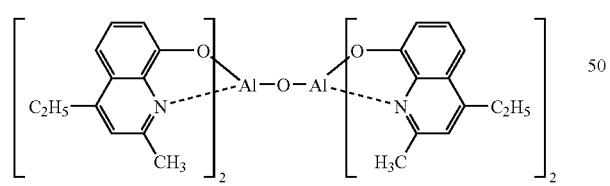
(123)
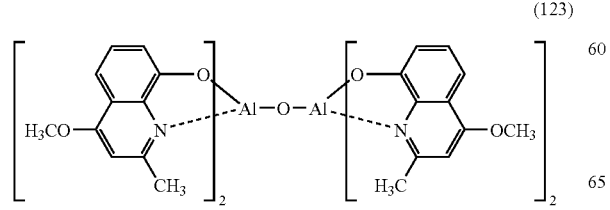
(124)
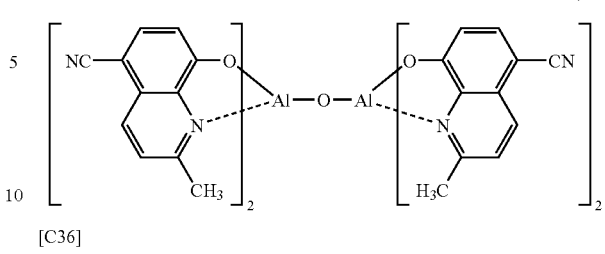
[C36]
(125)
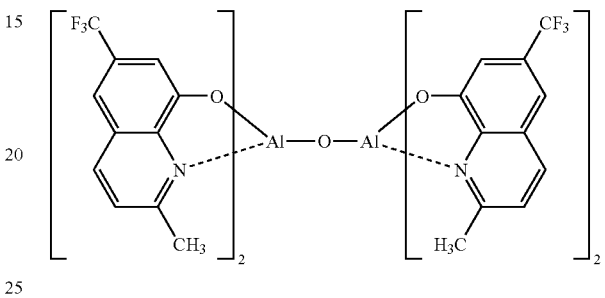
Furthermore, organic materials capable of transporting electrons and suitable for use in the electron transporting layer 6 may also be chosen from phenanthroline derivatives, for examples, Compounds (126)-(134) shown below.
[C37]
(126)
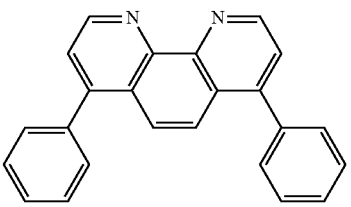
(127)
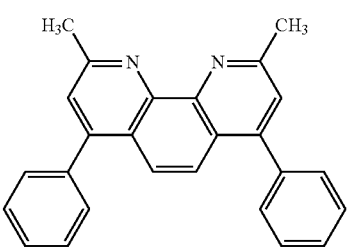
[C38]
(128)
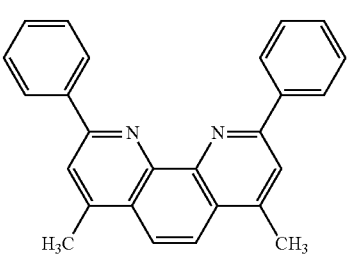

(129) 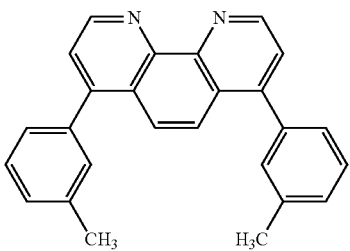

(130) 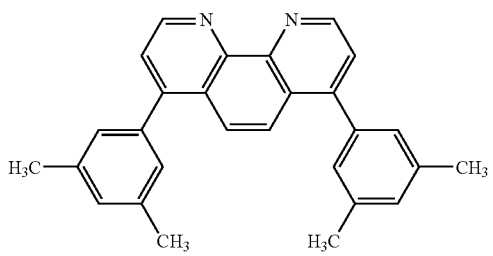

[C39]

(131) 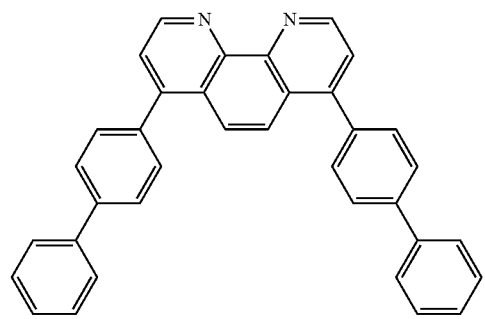

(132) 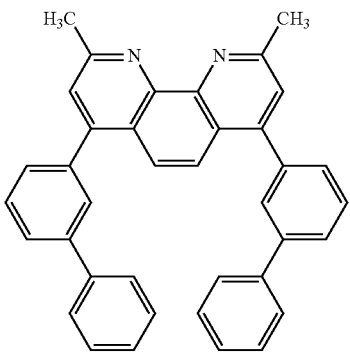

(133) 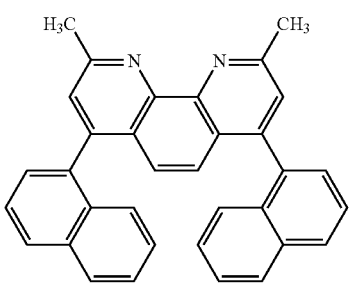

(134) 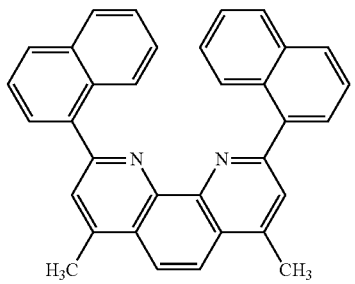

EXAMPLES

This invention will be described further in detail with reference to the accompanying examples. In the examples, % and ppm are expressed on weight basis. Halogen-containing compounds in phenolic compounds were analyzed by HPLC (limit of detection of Br compounds, 0.5 ppm). The analysis of an aluminum chelate complex for A1Q2X was carried out by determining the content of halogen in the aluminum chelate complex by ion chromatography (limit of detection, 50 ppm) and calculating A1Q2X from this halogen content.

Synthetic Example 1

In a three-necked flask equipped with a condenser, a thermometer and a stirrer were placed 26.8 g of 6-bromo-2-naphthol, 4.6 g of tetrakistriphenylphosphinepalladium and 100 ml of toluene and the mixture was stirred at 50° C. When the solids nearly dissolved, a solution of 14.6 g of phenylboronic acid in 100 ml of ethanol was added and stirred. When the solutions mixed with each other, a solution of 30 g of sodium carbonate in 100 ml of water was added, the mixture was heated to the reflux temperature and stirred for 1 hour. Upon completion of the reaction, dilute hydrochloric acid was added until the aqueous layer became weakly acidic, the organic layer was recovered and the solvent was distilled off under reduced pressure. The crude product was recrystallized from 50 ml of toluene and the crystals collected by filtration were washed with toluene and dried at 80° C. under reduced pressure to give 11.9 g of 6-phenyl-2-naphthol. The unreacted 6-bromo-2-naphthol was not detected by HPLC.

Synthetic Example 2

In a three-necked flask were placed 8.3 g of 2-methyl-8-quinolinol (purity, 98.0% or more), 10.7 g of aluminum isopropoxide and 290 ml of anhydrous ethanol and the mixture was heated to the reflux temperature in an atmosphere of nitrogen and stirred for 1 hour. The reaction mixture was cooled to room temperature and the insoluble matters were removed by filtration through Celite. To the filtrate was added slowly at room temperature with stirring a solution of 8.3 g of 2-methyl-8-quinolinol and 11.5 g of 6-phenyl-2-naphthol obtained in Synthetic Example 1 in 75 ml of anhydrous ethanol and the mixture was stirred for 1 hour. The precipitates were collected by filtration, washed with ethanol, then washed with methanol and dried at 70° C. under reduced pressure for 5 hours to give 27.9 g of Compound (14). Analysis by ion chromatography did not detect Br and the content of an impurity corresponding to Compound (14) whose phenyl group is replaced with Br or bis-(2-methyl-8-quinolinolato)

(6-bromo-2-naphtholato)-aluminum-(III) (hereinafter referred to as BQMA) was calculated to be less than 350 ppm.

Synthetic Example 3

In a three-necked flask were placed 17.9 g of 6-bromo-2-naphthol, 4.6 g of tetrakistriphenylphosphinepalladium and 200 ml of toluene and the mixture was stirred at room temperature. When the solids nearly dissolved, a solution of 9.8 g of phenylboronic acid in 200 ml of ethanol was added and stirred. Thereafter, a solution of 20 g of sodium carbonate in 200 ml of water was added and the mixture was stirred at room temperature for 1 hour. Upon completion of the reaction, dilute hydrochloric acid was added until the aqueous layer became weakly acidic, the organic layer was recovered and the solvent was distilled off under reduced pressure to give 22 g of 6-phenyl-2-naphthol. The amount of the unreacted 6-bromo-2-naphthol was 16%.

Synthetic Example 4

In a three-necked flask were placed 7.2 g of 2-methyl-8-quinolinol, 9.2 g of aluminum isopropoxide and 270 ml of anhydrous ethanol and the mixture was heated to the reflux temperature in an atmosphere of nitrogen and stirred for 1 hour. The reaction mixture was cooled to room temperature and the insoluble matters were removed by filtration through Celite. To the filtrate at room temperature was added slowly with stirring a solution of 7.2 g of 2-methyl-8-quinolinol and 9.9 g of 6-phenyl-2-naphthol obtained in Synthetic Example 3 in 50 ml of anhydrous ethanol and the mixture was stirred for 1 hour. The precipitates were collected by filtration, washed with ethanol, then washed with methanol and dried at 70° C. under reduced pressure for 5 hours to give 14 g of Compound (14). The content of Br in this compound was 2000 ppm and the content of BQMA was calculated to be 500 ppm.

Synthetic Example 5

Compound (14) obtained in Synthetic Example 2 was further purified by sublimation. The purification by sublimation of 2.0 g of the compound in question was carried out in an apparatus which was constructed of a glass outer tube and a glass inner tube and provided with a heating zone and a collecting zone. The collecting zone is cooled by nitrogen gas to be supplied. The system was evacuated to 2.0 Torr by a vacuum pump, the temperature of the heating zone was set at 360° C. and the compound was collected on the inner wall of glass in the collecting zone. The amount of Compound (14) thus collected in the collecting zone was 1.1 g, Br was not detected and the content of BQMA was calculated to be less than 350 ppm.

Synthetic Example 6

In a 300-ml three-necked flask were placed 4.33 g of 2-methyl-8-quinolinol, 5.56 g of aluminum isopropoxide and 160 ml of anhydrous ethanol and the mixture was heated to the reflux temperature in an atmosphere of nitrogen and stirred for 1 hour. The reaction mixture was cooled to room temperature and the insoluble matters were removed by filtration through Celite. To the filtrate at room temperature was added slowly with stirring a solution of 4.33 g of 2-methyl-8-quinolinol and 6.07 g of 6-bromo-2-naphthol in 30 ml of anhydrous ethanol and the mixture was stirred for 1 hour. The precipitates were collected by filtration, washed with ethanol, then washed with methanol and dried at 70° C. under reduced pressure for 5 hours to give 14 g of BQMA.

Synthetic Example 7

In a three-necked flask were placed 33 g of o-aminophenol and 207 g of concentrated hydrochloric acid and the mixture was heated to the reflux temperature and stirred for 1 hour. To the mixture being heated under reflux was slowly added 51 g of 3-penten-2-one with a purity of 65% over 2 hours and stirring was continued for another 2 hours. Upon completion of the reaction, the reaction mixture was cooled to room temperature, 300 ml of a 48% aqueous solution of NaOH was added until the aqueous phase became alkaline. Ethyl acetate was added further, the organic layer was recovered and the solvent was distilled off under reduced pressure. The crude product thus obtained was purified by gas chromatography, recrystallized from hexane and the crystals collected by filtration were washed with hexane and dried at 80° C. under reduced pressure to give 18.9 g of 2,4-dimethyl-8-quinolinol.

Synthetic Example 8

In a three-necked flask were placed 3.5 g of 2,4-dimethyl-8-qunolinol obtained in Synthetic Example 7, 4.1 g of aluminum isopropoxide and 150 ml of anhydrous ethanol and the mixture was heated to the reflux temperature in an atmosphere of nitrogen and stirred for 1 hour. The reaction mixture was cooled to room temperature and the insoluble matters were removed by filtration through Celite. To the filtrate at room temperature was added slowly with stirring a solution of 3.5 g of 2,4-dimethyl-8-quinolinol and 4.7 g of 6-phenyl-2-naphthol obtained in Synthetic Example 1 in 100 ml of anhydrous ethanol and the mixture was stirred for 1 hour. The precipitates were collected by filtration, washed with ethanol, then washed with methanol and dried at 70° C. under reduced pressure for 5 hours to give 9.0 g of Compound (23). Analysis by ion chromatography did not detect Br and the content of an impurity corresponding to a compound represented by general formula (2), that is, Compound (23) whose phenyl group is replaced with Br or bis-(2,4-dimethyl-8-quinolinolato)(6-bromo-2-naptholato)-aluminum-(III) (hereinafter referred to as BDQMA), was calculated to be less than 350 ppm.

Synthetic Example 9

In a three-necked flask were placed 26.8 g of 6-bromo-2-naphthol, 4.6 g of tetrakistriphenylphosphinepalladium and 100 ml of toluene and the mixture was stirred at 50° C. When the solids nearly dissolved, a solution of 20.6 g of 2-naphthaleneboronic acid in 100 ml of ethanol was added and stirred. When the solutions mixed with each other, a solution of 30 g of sodium carbonate in 100 ml of water was added, the mixture was heated to the reflux temperature and stirred for 1 hour. Upon completion of the reaction, dilute hydrochloric acid was added until the aqueous layer became weakly acidic, the organic layer was recovered and the solvent was distilled off under reduced pressure. The crude product was recrystallized from a mixture of toluene and ethyl acetate, the crystals were collected by filtration, washed with toluene and dried at 80° C. under reduced pressure to give 15.6 g of 6-(2-naphthyl)-2-naphthol. The unreacted 6-bromo-2-naphthol was not detected.

Synthetic Example 10

In a three-necked flask were placed 8.3 g of 2-methyl-8-quinolinol, 10.7 g of aluminum isopropoxide and 290 ml of anhydrous ethanol and the mixture was heated to the reflux temperature in an atmosphere of nitrogen and stirred for 1 hour. The reaction mixture was cooled to room temperature and the insoluble matters were removed by filtration through Celite. To the filtrate at room temperature was added slowly with stirring a solution of 8.3 g of 2-methyl-8-quinolinol and 14.1 g of 6-(2-naphthyl)-2-naphthol obtained in Synthetic Example 9 in 75 ml of anhydrous ethanol and stirred for 1 hour. The precipitates were collected by filtration, washed with ethanol, then washed with methanol and dried at 70° C. under reduced pressure for 5 hours to give 28.7 g of Compound (15). Br was not detected and the content of BQMA or Compound (15) whose naphthyl group is replaced with Br was calculated to be less than 350 ppm.

Synthetic Example 11

Compound (23) obtained in Synthetic Example 8 was further purified by sublimation by weighing out 2.0 g of the compound and using the apparatus for purification by sublimation used in Synthetic Example 5. The system was evacuated to 2.0 Torr by a vacuum pump, the temperature of the heating zone was set at 370° C. and the compound in question was collected on the inner wall of glass in the collecting zone. Compound (23) thus collected amounted to 1.2 g, Br was not detected and the content of the impurity BDQMA was calculated to be less than 350 ppm.

Synthetic Example 12

Compound (15) obtained in Synthetic Example 10 was further purified by sublimation by weighing out 2.0 g of the compound and using the apparatus for purification by sublimation used in Synthetic Example 5. The system was evacuated to 2.0 Torr by a vacuum pump, the temperature of the heating zone was set at 380° C. and the compound in question was collected on the inner wall of glass in the collecting zone. Compound (15) thus collected amounted to 1.1 g, Br was not detected and the content of the impurity BQMA was calculated to be less than 350 ppm.

Synthetic Example 13

In a three-necked flask were placed 3.5 g of 2,4-dimethyl-8-quinolinol obtained in Synthetic Example 7, 4.1 g of aluminum isopropoxide and 150 ml of anhydrous ethanol and the mixture was heated to the reflux temperature in an atmosphere of nitrogen and stirred for 1 hour. The reaction mixture was cooled to room temperature and the insoluble matters were removed by filtration through Celite. To the filtrate at room temperature was added slowly with stirring a solution of 3.5 g of 2,4-dimethyl-8-quinolinol and 4.5 g of 6-bromo-2-naphthol in 100 ml of anhydrous ethanol and the mixture was stirred for 1 hour. The precipitates were collected by filtration, washed with ethanol, then washed with methanol and dried at 70° C. under reduced pressure for 5 hours to give 14 g of BDQMA.

The following samples 1-5 were prepared from the compounds obtained in the aforementioned Synthetic Examples.

Sample 1: Compound (14) obtained in Synthetic Example 2
Sample 2: Compound (14) obtained in Synthetic Example 4
Sample 3: Compound (14) obtained in Synthetic Example 5
Sample 4: Compound (14) obtained in Synthetic Example 2 in which 1000 ppm of BQMA obtained in Synthetic Example 6 is incorporated
Sample 5: Compound (14) obtained in Synthetic Example 2 in which 10000 ppm of BQMA obtained in Synthetic Example 6 is incorporated
Sample 6: Compound (23) obtained in Synthetic Example 11
Sample 7: Compound (15) obtained in Synthetic Example 12
Sample 8: Compound (23) obtained in Synthetic Example 11 in which 1000 ppm of BDQMA obtained in Synthetic Example 13 is incorporated
Sample 9: Compound (15) obtained in Synthetic Example 12 in which 1000 ppm of BQMA obtained in Synthetic Example 6 is incorporated Samples 2, 4, 5, 8 and 9 are prepared for comparison.

Example 1

A hole injecting layer was formed by vacuum-depositing CuPc on an ITO anode at a rate of 3 Å/s to a thickness of 250 Å. A hole transporting layer was then formed on the hole injecting layer of CuPc by vacuum-depositing NPB at a rate of 3 Å/s to a thickness of 550 Å. Then, an emissive layer was formed on the hole transporting layer of NPB by co-vacuum-depositing from separate evaporation sources the aforementioned Sample 1 as an organic host material and the aforementioned Compound (31) or 2,3,7,8,12,13,17,18-octaethyl-21H,23H-phorphine platinum (II) (hereinafter referred to as PtOEP) as an organic guest material emitting red phosphorescence to a thickness of 475 Å. The concentration of the organic guest material in the emissive layer at this point was 7%.

Thereafter, an electron transporting layer was formed on the emissive layer by vacuum-depositing Alq3 at a rate of 3 Å/s to a thickness of 300 Å. An electron injecting layer was then formed on the electron transporting layer of Alq3 by vacuum-depositing lithium oxide ($Li_2O$) at a rate of 0.1 Å/s to a thickness of 10 Å and aluminum (Al) was vacuum-deposited on the electron injecting layer as cathode to a thickness of 1000 Å to give an organic EL element.

Example 2

An organic EL element was prepared as in Example 1 with the exception of using Sample 3 in place of Sample 1.

Comparative Examples 1-3

Organic EL elements were prepared as in Example 1 with the exception of using Sample 2, 4 or 5 in place of Sample 1 as an organic host material.

The organic EL elements obtained in the aforementioned Examples and Comparative Examples were operated at 7 $mA/cm^2$ and the time required for the luminance to attenuate 50% was determined. The results are shown in Table 1.

TABLE 1

|  | Sample | Time for 50% attenuation (hr) |
|---|---|---|
| Example 1 | 1 | 2000 |
| Example 2 | 3 | 3150 |
| Comp. Ex. 1 | 2 | 150 |

TABLE 1-continued

| Sample | Time for 50% attenuation (hr) |
|---|---|---|
| Comp. Ex. 2 | 4 | 18 |
| Comp. Ex. 3 | 5 | 1 |

It is seen from Table 1 that the content of the impurity BQMA is extremely closely related to the attenuation of light emission and the time for attenuation is prolonged markedly when this impurity is kept in the range of less than 350 ppm.

Example 3

A hole injecting layer was formed on an ITO anode by vacuum-depositing CuPc at a rate of 3 Å/s to a thickness of 250 Å. A hole transporting layer was then formed on the hole injecting layer of CuPc by vacuum-depositing NPB at a rate of 3 Å/s to a thickness of 550 Å. An emissive layer was formed on the hole transporting layer of NPB by co-vacuum-depositing from separate evaporation sources the aforementioned Sample 1 as an organic host material and PtOEP as an organic guest material emitting red phosphorescence to a thickness of 475 Å. The concentration of PtOEP in the emissive layer at this point was 7%.

Thereafter, an electron transporting layer was formed on the mixed emissive layer by vacuum-depositing Alq3 at a rate of 3 Å/s to a thickness of 300 Å. An electron injecting layer was formed on the electron transporting layer of Alq3 by vacuum-depositing lithium oxide at a rate of 0.1 Å/s to a thickness of 10 Å and aluminum was vacuum-deposited on the electron injecting layer as cathode to a thickness of 1000 Å to give an organic EL element.

Examples 4-5

Organic EL elements were prepared as in Example 3 with the exception of using Sample 6 or 7 in place of Sample 1.

Comparative Examples 4-8

Organic EL elements were prepared as in Example 3 with the exception of using Sample 2, 4, 5, 8 or 9 in place of Sample 1.

The organic EL elements obtained in the aforementioned Examples and Comparative Examples were operated at 5.5 mA/cm$^2$ and the time required for the luminance to attenuate 50% was determined. The results are shown in Table 2.

TABLE 2

| Sample | Time for 50% attenuation (hr) |
|---|---|---|
| Example 3 | 1 | 50000 |
| Example 4 | 6 | 40000 |
| Example 5 | 7 | 38000 |
| Comp. Ex. 4 | 2 | 1200 |
| Comp. Ex. 5 | 4 | 145 |
| Comp. Ex. 6 | 5 | 5 |
| Comp. Ex. 7 | 8 | 120 |
| Comp. Ex. 8 | 9 | 110 |

It is seen from Table 2 that the content of the impurity BQMA or BDQMA is extremely closely related to the attenuation of light emission and the time for attenuation is prolonged markedly when these impurities are kept in the range of less than 350 ppm.

What is claimed is:

1. A method for preparing an aluminum chelate complex for an organic EL element represented by general formula (1) which contains less than 350 wt ppm of a compound represented by general formula (2) as an impurity:

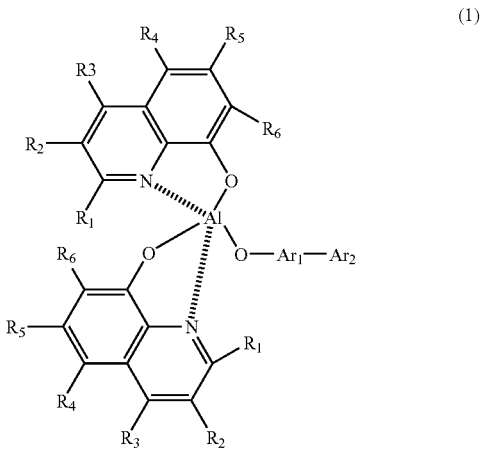

(1)

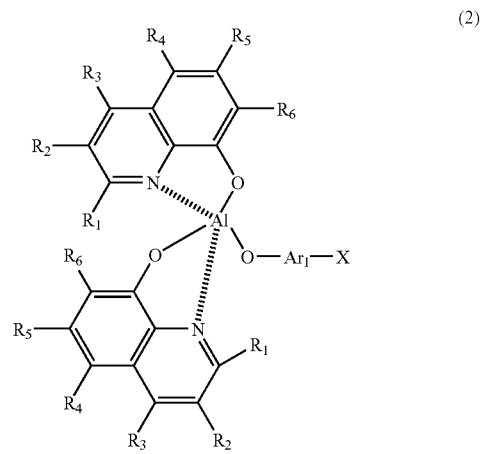

(2)

in general formulas (1) and (2), Ar$_1$ is naphthylene, Ar$_2$ is naphthyl or phenyl, the total number of aromatic rings in Ar$_1$ and Ar$_2$ is 3 to 4 and these aromatic rings may be condensed; R$_1$-R$_6$ are independently hydrogen or hydrocarbon groups containing 1-8 carbon atoms; and X is Br, Cl or I, said method comprising:

reacting aluminum isopropoxide successively with a quinolinol derivative and a phenolic compound represented by HO—Ar$_1$—Ar$_2$ which comprises purifying the quinolinol derivative and the phenolic compound in such a manner as to reduce the amount of a compound contained therein and represented by HO—Ar$_1$—X to 350 wt ppm or less and then submitting them to the reaction.

2. A method for preparing an aluminum chelate complex for an organic EL element represented by general formula (1) which contains less than 350 wt ppm of a compound represented by general formula (2) as an impurity:

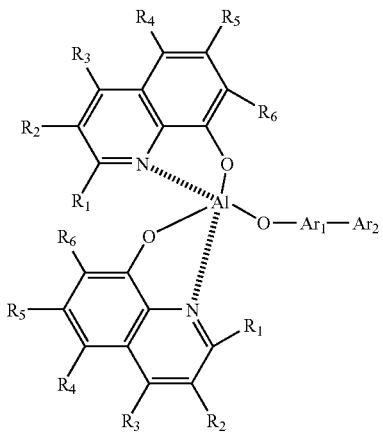

(1)

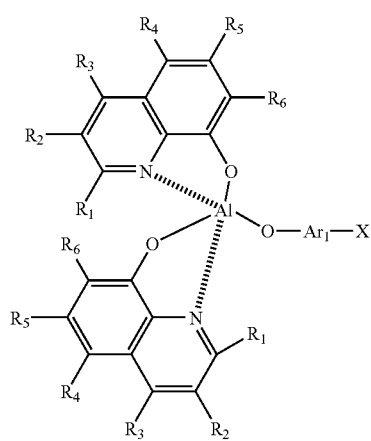

(2)

in general formulas (1) and (2), $Ar_1$ is a bicyclic arylene group, $Ar_2$ is a mono- or bicyclic aryl group, the total number of aromatic rings in $Ar_1$ and $Ar_2$ is 3 to 4 and these aromatic rings may be condensed; $R_1$-$R_6$ are independently hydrogen or hydrocarbon groups containing 1-8 carbon atoms; and X is a halogen, said method comprising:

reacting aluminum isopropoxide successively with a quinolinol derivative and a phenolic compound represented by HO—$Ar_1$—$Ar_2$ which comprises purifying the quinolinol derivative and the phenolic compound in such a manner as to reduce the amount of a compound contained therein and represented by HO—$Ar_1$—X to 350 wt ppm or less and then submitting them to the reaction.

3. A method for preparing an aluminum chelate complex for an organic EL element represented by general formula (1) which contains less than 350 wt ppm of a compound represented by general formula (2) as an impurity:

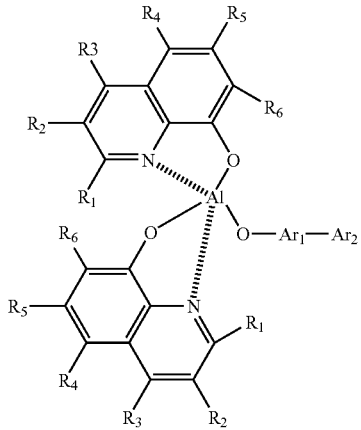

(1)

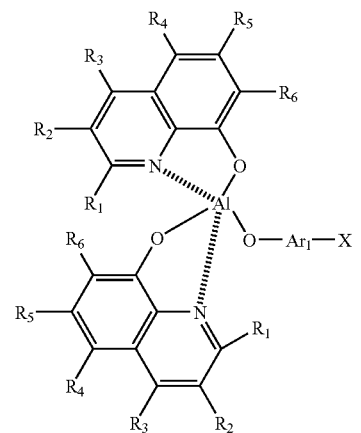

(2)

in general formulas (1) and (2), $Ar_1$ is a bicyclic arylene group, $Ar_2$ is a mono- or bicyclic aryl group, the total number of aromatic rings in $Ar_1$ and $Ar_2$ is 3 to 4 and these aromatic rings may be condensed; $R_1$-$R_6$ are independently hydrogen or hydrocarbon groups containing 1-8 carbon atoms; and X is a halogen, said method comprising:

reacting aluminum isopropoxide successively with a quinolinol derivative and a phenolic compound represented by HO—$Ar_1$—$Ar_2$ which comprises purifying by sublimation the crude aluminum chelate complex containing 350 wt ppm or more of a compound represented by general formula (2) after washing with or recrystallization from an organic solvent until the amount of said halogen-containing compound becomes 350 wt ppm or less.

4. A method for preparing an aluminum chelate complex as described in claim 2 which comprises reacting a compound represented by HO—$Ar_1$—X with a compound represented by $(Ar_2)a$-Y (wherein Y is Cu, X, Li, B(OH)$_2$, MgX, ZnX and SnMe$_3$, X is a halogen and a is an integer of 1-10) to form the phenolic compound represented by HO—$Ar_1$—$Ar_2$.

5. A method for preparing an aluminum chelate complex as described in claim 4 which comprises purifying by recrystallization the phenolic compound obtained by the reaction and represented by HO—$Ar_1$—$Ar_2$ and purifying by sublimation the aluminum chelate complex obtained from said phenolic compound.

6. A method for preparing an aluminum chelate complex as described in claim 3 which comprises reacting a compound represented by HO—Ar$_1$—X with a compound represented by (Ar$_2$)a-Y (wherein Y is Cu, X, Li, B(OH)$_2$, MgX, ZnX and SnMe$_3$, X is a halogen and a is an integer of 1-10) to form the phenolic compound represented by HO—Ar$_1$—Ar$_2$.

7. A method for preparing an aluminum chelate complex as described in claim 6 which comprises purifying by recrystallization the phenolic compound obtained by the reaction and represented by HO—Ar$_1$—Ar$_2$ and purifying by sublimation the aluminum chelate complex obtained from said phenolic compound.

* * * * *